US012714712B2

(12) United States Patent
Brooks et al.

(10) Patent No.: US 12,714,712 B2
(45) **Date of Patent: *Aug. 25, 2026**

(54) COMBINATION THERAPY WITH A MUTANT IDH INHIBITOR AND A Bcl-2 INHIBITOR

(71) Applicants: Eli Lilly and Company, Indianapolis, IN (US); Board of Regents, The University of Texas System, Austin, TX (US)

(72) Inventors: Nathan Arthur Brooks, Fishers, IN (US); Courtney DiNardo, Houston, TX (US); Raymond Gilmour, Indianapolis, IN (US); Marina Konopleva, Houston, TX (US); Vivian Salama, Houston, TX (US)

(73) Assignees: Eli Lilly and Company, Indianapolis, IN (US); Board of Regents, The University of Texas System, Austin, TX (US)

( * ) Notice: Subject to any disclaimer, the term of this patent is extended or adjusted under 35 U.S.C. 154(b) by 943 days.

This patent is subject to a terminal disclaimer.

(21) Appl. No.: 17/912,341

(22) PCT Filed: Mar. 22, 2021

(86) PCT No.: PCT/US2021/023442

§ 371 (c)(1),
(2) Date: Sep. 16, 2022

(87) PCT Pub. No.: WO2021/194950

PCT Pub. Date: Sep. 30, 2021

(65) Prior Publication Data

US 2023/0135992 A1 May 4, 2023

Related U.S. Application Data

(60) Provisional application No. 63/024,743, filed on May 14, 2020, provisional application No. 62/993,166, filed on Mar. 23, 2020.

(51) Int. Cl.

| | |
|---|---|
| ***A61K 31/5365*** | (2006.01) |
| ***A61K 9/00*** | (2006.01) |
| ***A61P 35/02*** | (2006.01) |
| ***C07K 16/28*** | (2006.01) |

(52) U.S. Cl.

CPC ........ *A61K 31/5365* (2013.01); *A61K 9/0019* (2013.01); *A61P 35/02* (2018.01); *C07K 16/28* (2013.01)

(58) Field of Classification Search

CPC ................................................. A61K 31/5365

See application file for complete search history.

(56) References Cited

U.S. PATENT DOCUMENTS 12,440,493 B2 * 10/2025 Brooks .............. A61K 31/5365

FOREIGN PATENT DOCUMENTS

| | | | |
|---|---|---|---|
| WO | 2013/046136 | A1 | 4/2013 |
| WO | 2016/171755 | A1 | 10/2016 |
| WO | 2017/019429 | A1 | 2/2017 |
| WO | 2017/213910 | A1 | 12/2017 |
| WO | 2018/111707 | A1 | 6/2018 |
| WO | 2019/222553 | A1 | 11/2019 |
| WO | 2021/194946 | A1 | 9/2021 |
| WO | 2021/194950 | A1 | 9/2021 |
| WO | 2021/194953 | A1 | 9/2021 |
| WO | 2022/020281 | A1 | 1/2022 |

OTHER PUBLICATIONS

Bayat Mokhtari, Reza et al. "Combination therapy in combating cancer." Oncotarget vol. 8,23 (2017): 38022-38043. doi:10.18632/oncotarget.16723 (Year: 2017).*

International Search Report of the International Searching Authority pertaining to International Application No. PCT/US2021/023442; Date of Mailing: Jul. 1, 2021; 6 pages.

Written Opinion of the International Searching Authority pertaining to International Application No. PCT/US2021/023442; Date of Mailing: Jul. 1, 2021; 8 pages.

McBride, A., Houtmann, S., Wilde, L., Vigil, C., Eischen, C. M., Kasner, M., & Palmisiano, N. (2019). The role of inhibition of apoptosis in acute leukemias and myelodysplastic syndrome. *Frontiers in oncology*, 9, article No. 192, pp. 1-11.

Choe, S. et al., Molecular Mechanisms Mediating Relapse Following Ivosidenib Monotherapy in Patients with IDH1-Mutant Relapsed or Refractory Acute Myeloid Leukemia, 61st American Society of Hematology Annual Meeting, Presentation 545, Dec. 9, 2019, 16 pages.

Rizzo, A. et al., Second-Line Treatment in Advanced Biliary Tract Cancer: Today and Tomorrow, Anticancer Research, 2020, 3013-3030, 40 (6).

Paschka, P. et al., IDH1 and IDH2 Mutations Are Frequent Genetic Alterations in Acute Myeloid Leukemia and Confer Adverse Prognosis in Cytogenetically Normal Acute Myeloid Leukemia With NPM1 Mutation Without FLT3 Internal Tandem Duplication, J. Clin. Oncol., 2010, 3636-3643, 28 (22).

(Continued)

*Primary Examiner* — Andrew D Kosar
*Assistant Examiner* — Connor K English
(74) *Attorney, Agent, or Firm* — Nielsen IP Law LLC

(57) ABSTRACT

The present invention relates to combination therapy with a mutant IDH inhibitor of Formula (I) and Bcl-2 inhibitor, for the treatment of cancer.

(I)

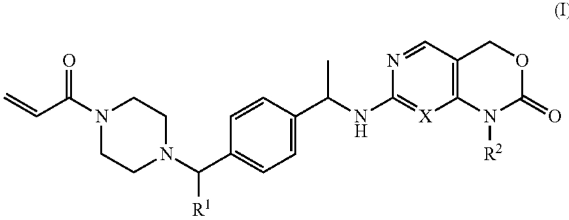

10 Claims, No Drawings

(56) References Cited

OTHER PUBLICATIONS

Fiorentini, A. et al., The Time Has Come for Targeted Therapies for AML: Lights and Shadows, Oncology and Therapy, 2020, 13-32, 8 (1).
Brooks, N. et al., Identification and Characterization of LY3410738, a Novel Covalent Inhibitor of Cancer-Associated Mutant Isocitrate Dehydrogenase 1 (IDH1), 2019, Cancer Res., 79 (13_Supplement): LB-274.
Brooks, N. et al., Identification and Characterization of LY3410738, a Novel Covalent Inhibitor of Cancer-Associated Mutant Isocitrate Dehydrogenase 1 (IDH1), 2019, [poster]. In: Proceedings of the American Association for Cancer Research Annual Meeting 2019; Mar. 29-Apr 3, 2019; Atlanta, GA.
Salama, V. et al., LY3410738, A Novel Inhibitor of Mutant IDH1 is More Effective Than Ivosidenib and Potentiates Antileukemic Activity of Standard Chemotherapy in Preclinical Models of Acute Myeloid Leukemia (AML), 2020, Cancer Res., 80 (16_ Supplement): 6417.
Salama, V. et al., LY3410738, A Novel Inhibitor of Mutant IDH1 is More Potent Than Ivosidenib (AG-120) and Potentiates Antileukemic Activity of Standard Chemotherapy in Preclinical Models of Acute Myeloid Leukemia (AML), 2020, [poster 8463]. In: Proceedings of the Annual Meeting of the American Association for Cancer Research 2020; Apr. 27-28, 2020 and Jun 22-24. Philadelphia (PA).
Stein, E. M. et al., A Phase 1 Study of LY3410738, a First-in-Class Covalent Inhibitor of Mutant IDH in Advanced Myeloid Malignancies (Trial in Progress), 2020, [poster 2877], 62nd ASH Annual Meeting and Exposition; San Diego, CA; Dec. 5-8, 2020.
Stein, E. M. et al., A Phase 1 Study of LY3410738, a First-in-Class Covalent Inhibitor of Mutant IDH in Advanced Myeloid Malignancies (Trial in Progress), 2020, Blood, 136 (Supplement 1) 26.
Pauff, J. M. et al., A Phase 1 Study of LY3410738, a First-in-Class Covalent Inhibitor of Mutant IDH1 in Cholangiocarcinoma and Other Advanced Solid Tumors, 2021, Journal of Clinical Oncology, 39, 3.
Pauff, J. M. et al., A Phase 1 Study of LY3410738, a First-in-Class Covalent Inhibitor of Mutant IDH1 in Cholangiocarcinoma and Other Advanced Solid Tumors, 2021, [poster TPS350], ASCO GI Cancers Symposium, San Francisco, CA Jan. 15-17, 2021.
NCT04603001, Protocol ID: LOXO-IDH-20001, Study of Oral LY3410738 in Patients With Advanced Hematologic Malignancies With IDH1 or IDH2 Mutations, Submitted Date: Oct. 21, 2020 (v1); First Posted Oct. 26, 2020; ClinicalTrials.gov, https://classic.clinicaltrials.gov/ct2/history/NCT04603001?V_1=View#StudyPageTop.
NCT04521686, Protocol ID: LOXO-IDH-20002, Study of LY3410738 Administered to Patients With Advanced Solid Tumors With IDH1 Mutations, Submitted Date: Aug. 18, 2020 (v1); First Posted Aug. 20, 2020; ClinicalTrials.gov, https://classic.clinicaltrials.gov/ct2/history/NCT04521686?V_1=View#StudyPageTop.
International Search Report, International Application No. PCT/US2021/023436, dated Jul. 1, 2021, 4 pages.
Written Opinion of the International Searching Authority, International Application No. PCT/US2021/023436, dated Jul. 1, 2021, 6 pages.
International Search Report, International Application No. PCT/US2021/023452, dated Jul. 14, 2021, 5 pages.
Written Opinion of the International Searching Authority, International Application No. PCT/US2021/023452, dated Jul. 14, 2021, 5 pages.
International Search Report, International Application No. PCT/US2021/042268, dated Nov. 2, 2021, 4 pages.
Written Opinion of the International Searching Authority, International Application No. PCT/US2021/042268, dated Nov. 2, 2021, 7 pages.
Communication under Rule 71(3) Epc, Ep Application No. 21719346.5, dated Nov. 9, 2023, 30 pages.
First Office Action, CN Application No. 202180024301.6, dated Apr. 22, 2023, 3 pages.
Observation on the First Office Action, CN Application No. 202180024301.6, dated Sep. 5, 2023, 3 pages.
Second Office Action, CN Application No. 202180024301.6, dated Dec. 7, 2023, 2 pages.
Office Action, CA Application No. 3,172,663, dated Jan. 15, 2024, 5 pages.
Examination report No. 1 for standard patent application, AU Application No. 2021241470, dated Aug. 23, 2023, 3 pages.
Response to Examination Report, AU Application No. 2021241470, dated Nov. 16, 2023, 11 pages.
Notice of acceptance for patent application, AU Application No. 2021241470, dated Dec. 5, 2023, 3 pages.
Office Action, EA Application No. 202292411, dated Nov. 10, 2023, 3 pages.
Certificate of Grant, AU Application No. 2021241470, dated Mar. 28, 2024, 1 page.
Notice of Grant for Patent, AU Application No. 2021241470, dated Mar. 28, 2024, 1 page.
Response to Office Action, CA Application No. 3172663, dated May 13, 2024, 14 pages.

* cited by examiner

COMBINATION THERAPY WITH A MUTANT IDH INHIBITOR AND A Bcl-2 INHIBITOR

The present invention relates to combination therapy with a mutant isocitrate dehydrogenase (IDH) inhibitor and Bcl-2 inhibitor, for the treatment of cancer.

IDH and IDH2 are enzymes that catalyze the conversion of isocitrate to α-ketoglutarate (α-KG), and reduces nicotinamide adenine dinucleotide phosphate ($NADP^+$) to NADPH (Megias-Vericat J, et al., *Blood Lymph. Cancer: Targets and Therapy* 2019; 9: 19-32).

Neomorphic (de novo) mutations in IDH1, e.g., at IDH1 amino acid residue R132, contribute to tumorigenesis in several types of cancer, including solid tumor cancers and hematologic malignancies (Badur M G, et al., *Cell Reports* 2018; 25: 1680). IDH1 mutations can result in high levels of 2-hydroxyglutarate (2-HG), which inhibits cellular differentiation, and inhibitors of mutant IDH1 can reduce 2-HG levels, which promotes cellular differentiation (Molenaar R J, et al., *Oncogene* 2018; 37: 1949-1960). Mutations also occur in IDH2, e.g., at amino acid residues R172, R140 and R172 (Yang H, et al., *Clin. Cancer. Res.* 2012; 18: 5562-5571; Mondesir J, et al., *J. Blood Med.* 2016; 7: 171-180).

For example, acute myeloid leukemia (AML) is characterized by a diverse spectrum of mutated genes and a multi-clonal genomic architecture comprising preleukemic and leukemic clones that evolve dynamically over time and under the selective pressure of therapy (Bloomfield C D, et al., *Blood Revs.* 2018; 32: 416-425). Induction chemotherapy with cytarabine and an anthracycline ("7+3") has been the standard of care for more than 4 decades for subjects with newly diagnosed AML.

In recent years, five additional drugs have been approved by the U.S. Food and Drug Administration for treating AML: midostaurin, enasidenib, CPX-351, gemtuzumab ozogamicin (Bloomfield C D, et al., *Blood Revs.* 2018; 32: 416-425), and ivosidenib (Megias-Vericat J, et al., *Blood Lymph. Cancer: Targets and Therapy* 2019; 9: 19-32). Approximately 60% to 70% of adults with AML can be expected to attain complete remission (CR) status following appropriate induction therapy, and more than 25% of adults with AML (about 45% of those who attain CR) can be expected to survive 3 or more years and may be cured.

However, IDH1 resistance mutations are observed in 7-14% of AML subjects, and the associated high 2-HG level can result in an epigenetic hyper-methylation phenotype and a block in differentiation, resulting in leukemogenesis (Megias-Vericat J, et al., *Blood Lymph. Cancer: Targets and Therapy* 2019; 9: 19-3). In addition, mutations in the Flt3 kinase are observed in approximately one third of AML subjects (Lee H J, et al., *Oncotarget* 2018; 9: 924-936).

Thus, there remains a need for alternative mutant IDH-related cancer therapies.

Certain mutant IDH1 and IDH2 inhibitors are disclosed in WO 2018/111707 A1, including a compound defined herein as "Compound A," which is a covalent inhibitor of mutant IDH1 that modifies a single cysteine (Cys269) in an allosteric binding pocket, rapidly inactivates the enzyme, and selectively inhibits 2-HG production, without affecting α—KG levels (WO 2018/111707 A1).

The present invention provides a method of treating cancer, comprising administering to a human cancer subject having an IDH mutation a therapeutically effective amount of (a) a first compound of Formula I:

I

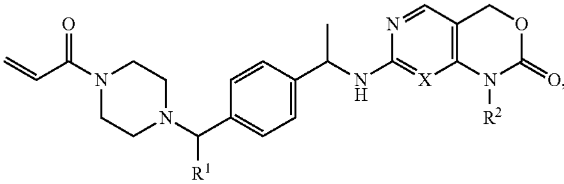

wherein:

$R^1$ is $—CH_2CH(CH_3)_2$, $—CH_2CH_3$, $—CH_2CH_2OCH_3$, or $—CH_2$-cyclopropyl;

$R^2$ is $—CH_3$ or $—CH_2CH_3$; and

X is N or CH, or a pharmaceutically acceptable salt thereof; and (b) a second compound that is a Bcl-2 inhibitor, or a pharmaceutically acceptable salt thereof.

In one embodiment, the IDH mutation is an IDH1 mutation or an IDH2 mutation. In another embodiment, the IDH mutation is an IDH1 mutation. In another embodiment, the IDH1 mutation is an IDH1 R132 mutation. In another embodiment, the IDH1 mutation is R132H, R132C, R132G, R132L, or R132S. In another embodiment, the IDH1 R132 mutation is R132H. In another embodiment, the IDH1 mutation is R132C. In another embodiment, the IDH1 mutation is R132G. In another embodiment, the IDH1 mutation is R132L. In another embodiment, the IDH1 mutation is R132S.

In another embodiment, the IDH mutation is an IDH2 mutation. In another embodiment, the IDH2 mutation is an IDH2 R140 mutation or an IDH2 R172 mutation. In another embodiment, the IDH2 mutation is an R140 mutation. In another embodiment, the R140 mutation is R140Q, R140L, or R140W. In another embodiment, the IDH2 mutation is an R172 mutation. In another embodiment, the R172 mutation is R172K, R172M, R172G, R172S or R172W.

In one embodiment of the method of the invention, in the first compound of Formula I, or a pharmaceutically acceptable salt thereof, X is N.

In another embodiment, in the first compound of Formula I, or a pharmaceutically acceptable salt thereof, X is N, $R^1$ is $—CH_2$-cyclopropyl, and $R^2$ is $—CH_2CH_3$. In another embodiment, in the first compound of Formula I, X is N, $R^1$ is $—CH_2$-cyclopropyl, and $R^2$ is $—CH_2CH_3$ In another embodiment, the first compound is:

7-[[(1S)-1-[4-[(1R)-2-cyclopropyl-1-(4-prop-2-enoylpiperazin-1-yl)ethyl]phenyl]ethyl]amino]-1-ethyl-4H-pyrimido[4,5-d][1,3]oxazin-2-one;

7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one; or 1-Ethyl-7-[[(1S)-1-[4-[1-(4-prop-2-enoylpiperazin-1-yl)propyl]phenyl]ethyl]amino]-4H-pyrimido[4,5-d][1,3]oxazin-2-one;

or a pharmaceutically acceptable salt thereof.

In another embodiment, the first compound is 7-[[(1S)-1[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

In another embodiment, the first compound is:

Compound A

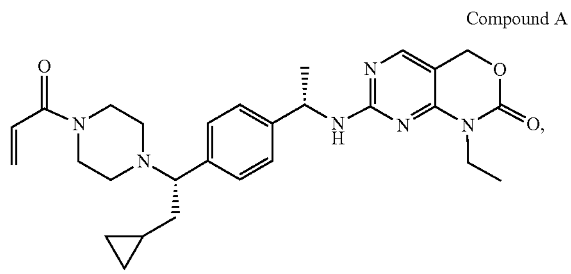 [SMILES: C=CC(=O)N1CCN([C@@H](CC2CC2)c2ccc([C@H](C)Nc3ncc4c(n3)N(CC)C(=O)OC4)cc2)CC1]

or a pharmaceutically acceptable salt thereof. In another embodiment, the first compound is Compound A.

In another embodiment, the subject is identified as having an IDH mutation. In another embodiment, the subject is identified as having an IDH mutation in tissue. In another embodiment, the subject is identified as having an IDH1 mutation. In another embodiment, the subject is identified as having an IDH2 mutation.

In another embodiment, the subject is identified as having an R132 IDH1 mutation. In another embodiment, the subject is identified as having an R132 IDH1 mutation in tissue. In another embodiment, the subject is identified as having an IDH2 mutation, e.g., an IDH2 R172, R140 or R172 mutation. In another embodiment, the subject is identified as having an IDH2 R172, R140 or R172 mutation in tissue.

In another embodiment, the cancer is a hematologic malignancy, and the subject is identified as having an IDH mutation (e.g., an IDH1 R132 mutation or an IDH2 R172, R140 or R172 mutation) in blood, bone marrow, lymph node, lymphatic fluid. In another embodiment, the subject is identified as having an IDH mutation (e.g., an IDH1 R132 mutation or an IDH2 R172, R140 or R172 mutation) in blood cells, bone marrow cells, lymph node cells or lymphatic fluid cells.

In another embodiment, the cancer is a solid tumor cancer, and the subject is identified as having an IDH mutation (e.g., an IDH1 R132 mutation or an IDH2 R172, R140 or R172 mutation) in solid tumor tissue. In another embodiment, the subject is identified as having an IDH mutation (e.g., an IDH1 R132 mutation or an IDH2 R172, R140 or R172 mutation) in solid tumor tissue cells.

In another embodiment, the first compound, or the pharmaceutically acceptable salt thereof, is administered before the second compound, or a pharmaceutically acceptable salt thereof.

In another embodiment, the first compound, or the pharmaceutically acceptable salt thereof, is administered after the second compound, or a pharmaceutically acceptable salt thereof.

In another embodiment, the first compound, or the pharmaceutically acceptable salt thereof, is co-formulated with the second compound, or a pharmaceutically acceptable salt thereof.

In another embodiment of the method of the invention, the cancer is a solid tumor cancer. In another embodiment, the solid tumor cancer is cholangiocarcinoma, head & neck cancer, chondrosarcoma, hepatocellular carcinoma, melanoma, pancreatic cancer, astrocytoma, oligodendroglioma, glioma, glioblastoma, bladder carcinoma, colorectal cancer, lung cancer, or sinonasal undifferentiated carcinoma. In another embodiment, the lung cancer is non-small cell lung cancer. In another embodiment, the solid tumor cancer is cholangiocarcinoma.

In another embodiment, the cancer is a hematologic malignancy. In another embodiment, the hematologic malignancy is acute myeloid leukemia, myelodysplastic syndrome myeloproliferative neoplasm, angioimmunoblastic T-cell lymphoma, T-cell acute lymphoblastic leukemia, polycythemia vera, essential thrombocythemia, primary myelofibrosis, or chronic myelogenous leukemia. In another embodiment, the hematologic malignancy is acute myeloid leukemia.

The present invention also provides a compound of Formula I:

I

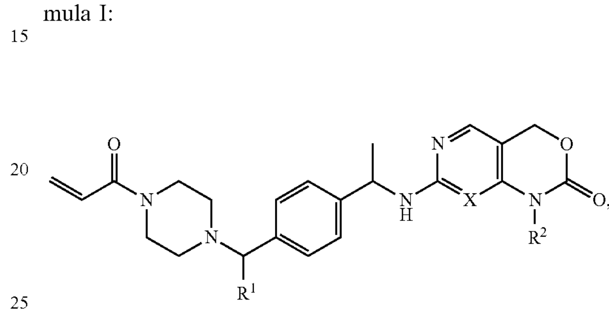

wherein:

$R^1$ is $—CH_2CH(CH_3)_2$, $—CH_2CH_3$, $—CH_2CH_2OCH_3$, or $—CH_2$-cyclopropyl;

$R^2$ is $—CH_3$ or $—CH_2CH_3$;

X is N or CH; or a pharmaceutically acceptable salt thereof; for use in combination with a Bcl-2 inhibitor, or a pharmaceutically acceptable salt thereof, in the treatment of cancer in a human subject having an IDH mutation in blood cells, bone marrow cells, or blood and bone marrow cells.

In one embodiment, the IDH mutation is an IDH1 mutation or an IDH2 mutation. In another embodiment, the IDH mutation is an IDH1 mutation. In another embodiment, the IDH1 mutation is an IDH1 R132 mutation. In another embodiment, the IDH1 mutation is R132H, R132C, R132G, R132L, or R132S. In another embodiment, the IDH1 R132 mutation is R132H. In another embodiment, the IDH1 mutation is R132C. In another embodiment, the IDH1 mutation is R132G. In another embodiment, the IDH1 mutation is R132L. In another embodiment, the IDH1 mutation is R132S.

In another embodiment, the IDH mutation is an IDH2 mutation. In another embodiment, the IDH2 mutation is an IDH2 R140 mutation or an IDH2 R172 mutation. In another embodiment, the IDH2 mutation is an R140 mutation. In another embodiment, the R140 mutation is R140Q, R140L, or R140W. In another embodiment, the IDH2 mutation is an R172 mutation. In another embodiment, the R172 mutation is R172K, R172M, R172G, R172S or R172W.

In one embodiment, the subject is identified as having an IDH mutation (e.g., an IDH1 R132 mutation or an IDH2 R172, R140 or R172 mutation).

In one embodiment the compound for use is of Formula I, wherein X is N, or a pharmaceutically acceptable salt thereof. In another embodiment, the compound for use is of Formula I, wherein $R^1$ is $—CH_2$-cyclopropyl, or a pharmaceutically acceptable salt thereof. In another embodiment, the compound for use is of Formula I, wherein $R^2$ is $—CH_2CH_3$, or a pharmaceutically acceptable salt thereof. In another embodiment, the compound for use is of Formula I, wherein X is N, $R^1$ is $—CH_2$-cyclopropyl, and $R^2$ is —$CH_2CH_3$, or a pharmaceutically acceptable salt thereof. In another embodiment, the compound is of Formula I, wherein X is N, $R^1$ is —$CH_2$-cyclopropyl, and $R^2$ is —$CH_2CH_3$.

In another embodiment, the compound is:

7-[[(1S)-1[4-[(1R)-2-Cyclopropyl-1-(4-prop-2-enoylpiperazin yl)ethyl]phenyl]ethyl]amino]-1-ethyl-4H-pyrimido[4,5-d][1,3]oxazin-2-one;

7-[[(1S)-1-[4-[(1S)-2-cyclopropyl-1-(4-prop-2-enoylpiperazin yl)ethyl]phenyl]ethyl]amino]-1-ethyl-4H-pyrimido[4,5-d][1,3]oxazin-2-one; or 1-Ethyl-7-[[(1S)-1-[4-[1-(4-prop-2-enoylpiperazin yl)propyl]phenyl]ethyl]amino]-4H-pyrimido[4,5-d][1,3]oxazin-2-one;

or a pharmaceutically acceptable salt thereof.

In another embodiment, the compound is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one, or a pharmaceutically acceptable salt thereof.

In another embodiment, the compound is:

(Compound A)

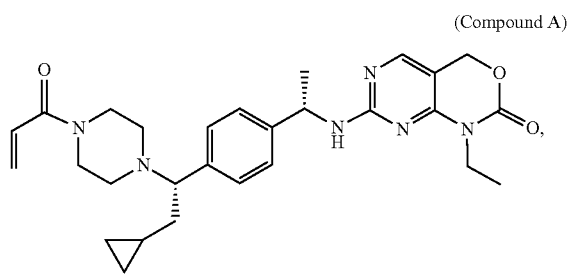 [SMILES: C=CC(=O)N1CCN([C@@H](CC2CC2)c2ccc([C@H](C)Nc3ncc4c(n3)N(CC)C(=O)OC4)cc2)CC1]

or a pharmaceutically acceptable salt thereof.

In another embodiment, the compound is Compound A.

Novel methods for use of the combination of a compound of Formula I and a Bcl-2 inhibitor to treat cancer are presented herein. Accordingly, some aspects of the present invention provide for a compound of Formula I for use in simultaneous, separate, or sequential combination with a Bcl-2 inhibitor in the treatment of cancer. Additionally, some aspects of the present invention provide for a compound of Formula I for use in simultaneous, separate, or sequential combination with a Bcl-2 inhibitor in the treatment of a solid tumor cancer. Moreover, some aspects of the present invention provide for a compound of Formula I for use in simultaneous, separate, or sequential combination with a Bcl-2 inhibitor in the treatment of a hematologic malignancy.

The present invention also provides a pharmaceutical composition comprising a compound of Formula I, for use in treating cancer in a human subject having an IDH mutation in blood cells, bone marrow cells, lymph node or lymphatic fluid.

In one embodiment, the IDH mutation is an IDH1 mutation or an IDH2 mutation. In another embodiment, the IDH mutation is an IDH1 mutation. In another embodiment, the IDH1 mutation is an IDH1 R132 mutation. In another embodiment, the IDH1 mutation is R132H, R132C, R132G, R132L, or R132S. In another embodiment, the IDH1 R132 mutation is R132H. In another embodiment, the IDH1 mutation is R132C. In another embodiment, the IDH1 mutation is R132G. In another embodiment, the IDH1 mutation is R132L. In another embodiment, the IDH1 mutation is R132S.

In another embodiment, the IDH mutation is an IDH2 mutation. In another embodiment, the IDH2 mutation is an IDH2 R140 mutation or an IDH2 R172 mutation. In another embodiment, the IDH2 mutation is an R140 mutation. In another embodiment, the R140 mutation is R140Q, R140L, or R140W. In another embodiment, the IDH2 mutation is an R172 mutation. In another embodiment, the R172 mutation is R172K, R172M, R172G, R172S or R172W.

The present invention also provides the use of a compound of Formula I, in the manufacture of a medicament for the treatment of cancer in a human subject identified as having an IDH mutation (e.g., an IDH1 R132 mutation or an IDH2 R172, R140 or R172 mutation) in blood, bone marrow, lymph node, lymphatic fluid, blood cells, bone marrow cells, lymph node cells or lymphatic fluid cells.

In one embodiment of the method of the invention, the cancer is frontline cancer. In another embodiment, the frontline cancer is a solid tumor cancer. In another embodiment, the frontline cancer is hematologic malignancy. In another embodiment, the frontline hematologic malignancy is frontline AML.

In another embodiment of the method of the invention, the cancer is relapsed cancer. In another embodiment, the relapsed cancer is a solid tumor cancer. In another embodiment, the relapsed cancer is hematologic malignancy. In another embodiment, the relapsed hematologic malignancy is relapsed AML.

In another embodiment of the method of the invention, the cancer is refractory cancer. In another embodiment, the refractory cancer is a solid tumor cancer. In another embodiment, the refractory cancer is hematologic malignancy. In another embodiment, the refractory hematologic malignancy is refractory AML.

In another embodiment of the method of the invention, the cancer is advanced cancer. In another embodiment, the advanced cancer is an advanced solid tumor cancer. In another embodiment, the advanced cancer is an advanced hematologic malignancy. In another embodiment, the advanced hematologic malignancy is advanced AML In another embodiment, the AML is acute promyelocytic leukemia.

In one embodiment of the of the method of the invention, the Bcl-2 inhibitor is venetoclax, obatoclax, navitoclax, or a pharmaceutically acceptable salt of any one of them. In another embodiment, the Bcl-2 inhibitor is venetoclax, or a pharmaceutically acceptable salt thereof. In another embodiment, the Bcl-2 inhibitor is venetoclax.

The present invention also provides a method of identifying a human subject for treatment with (a) a first compound of Formula I:

I

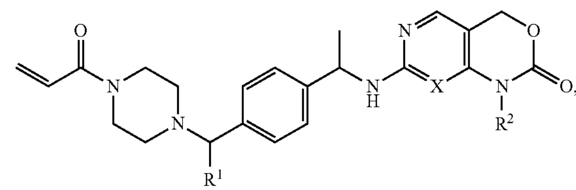

wherein:

$R^1$ is —$CH_2CH(CH_3)_2$, —$CH_2CH_3$, —$CH_2CH_2OCH_3$, or —$CH_2$-cyclopropyl;

$R^2$ is —$CH_3$ or —$CH_2CH_3$; and

X is N or CH, or a pharmaceutically acceptable salt thereof; and (b) a second compound that is a Bcl-2 inhibitor, or a pharmaceutically acceptable salt thereof, the method comprising identifying a human subject having a cancer and determining if the human subject has IDH mutation in blood, bone marrow, lymph node, lymphatic fluid, blood cells, bone marrow cells, lymph node cells, lymphatic fluid cells, or solid tissue, wherein the subject has a cancer.

In one embodiment, the IDH mutation is an IDH1 mutation or an IDH2 mutation. In another embodiment, the IDH mutation is an IDH1 mutation. In another embodiment, the IDH1 mutation is an IDH1 R132 mutation. In another embodiment, the IDH1 mutation is R132H, R132C, R132G, R132L, or R132S. In another embodiment, the IDH1 R132 mutation is R132H. In another embodiment, the IDH1 mutation is R132C. In another embodiment, the IDH1 mutation is R132G. In another embodiment, the IDH1 mutation is R132L. In another embodiment, the IDH1 mutation is R132S.

In another embodiment, the IDH mutation is an IDH2 mutation. In another embodiment, the IDH2 mutation is an IDH2 R140 mutation or an IDH2 R172 mutation. In another embodiment, the IDH2 mutation is an R140 mutation. In another embodiment, the R140 mutation is R140Q, R140L, or R140W. In another embodiment, the IDH2 mutation is an R172 mutation. In another embodiment, the R172 mutation is R172K, R172M, R172G, R172S or R172W.

In one embodiment of the method of the invention of identifying a human cancer subject for treatment, in the first compound of Formula I, X is N, or a pharmaceutically acceptable salt thereof. In another embodiment, in the first compound of Formula I, X is N, $R^1$ is —$CH_2$-cyclopropyl, and $R^2$ is —$CH_2CH_3$, or a pharmaceutically acceptable salt thereof. In another embodiment, in the first compound, X is N, le is —$CH_2$-cyclopropyl, and $R^2$ is —$CH_2CH_3$.

In another embodiment of the method of identifying a human cancer subject for treatment, the first compound is:

7-[[(1S)-1-[4-[(1R)-2-cyclopropyl-1-(4-prop-2-enoylpiperazin-1-yl)ethyl]phenyl]ethyl]amino]-1-ethyl-4H-pyrimido[4,5-d][1,3]oxazin-2-one;

7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one; or 1-Ethyl-7-[[(1S)-1-[4-[1-(4-prop-2-enoylpiperazin-1-yl)propyl]phenyl]ethyl]amino]-4H-pyrimido[4,5-d][1,3]oxazin-2-one; or a pharmaceutically acceptable salt thereof.

In another embodiment, the first compound is 7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one.

In another embodiment, the first compound is:

(Compound A)

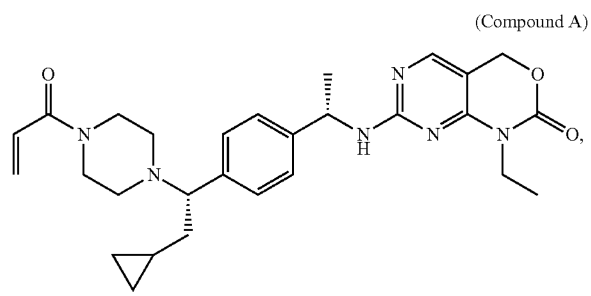 [SMILES: C=CC(=O)N1CCN([C@@H](CC2CC2)c2ccc([C@H](C)Nc3ncc4c(n3)N(CC)C(=O)OC4)cc2)CC1]

or a pharmaceutically acceptable salt thereof. In another embodiment, the first compound is Compound A.

Methods for assaying mutant IDH1 and IDH2 enzyme activity are known to those of ordinary skill in the art, e.g., in WO 2018/111707 A1.

As used above, and throughout the description of the invention, the following terms, unless otherwise indicated, shall be understood to have the following meanings:

The term "hematologic tissue" refers to blood, bone marrow, spleen, lymph node, or lymphatic fluid.

The term "solid tumor tissue" refers to tissue that is not hematologic tissue. Non-limiting examples of solid tissue are cholangial tissue, pancreatic tissue, head tissue, neck tissue, hepatic tissue, skin tissue, astrocytomal tissue, oligodendroglial tissue, glial tissue, brain tissue, bladder tissue, colorectal tissue, and lung tissue.

As used herein, a "Bcl-2 inhibitor" is a compound that binds to Bcl-2, and results in one or more of cytotoxicity in cancer cells, downregulation of Bcl-2 expression in cancer cells, mitochondrial dysfunction in cancer cells, and apoptosis in cancer cells. Methods for determining those effects are known to those of ordinary skill in the art, e.g., in Wen M, et al., *Front. Pharmacol.* 2019; 10: 391.

The term "mutant IDH inhibitor" refers to a compound that inhibits the enzyme activity of and/or the production of 2-HG by a mutant IDH enzyme (e.g., a mutant IDH1 enzyme or a mutant IDH2 enzyme). Methods for assaying mutant IDH1 and mutant IDH2 enzyme activity are known to those of ordinary skill in the art, e.g., in WO 2018/111707 A1. In the term "mutant IDH inhibitor, the word "mutant" refers to the IDH gene, not the inhibitor.

The term "solid tumor cancer" means that the cancer originated in a tissue that is not blood or bone marrow.

The term "hematologic malignancy" relates to cancer that originated in the blood, bone marrow, lymph node or lymphatic fluid.

The term "frontline cancer" means that the human cancer subject has never been treated for the cancer being treated.

The term "refractory cancer" refers to cancer that has been treated, but the human cancer subject did not respond to treatment.

The term "relapsed cancer" means that the human cancer subject responded to treatment for a period of time, but that the cancer has reoccurred.

The term "advanced cancer" refers to cancer that has spread to lymph nodes or to other tissues outside of the cancer's point of origin. For example, AML is AML that has spread to a tissue outside of the blood or the bone marrow.

The term "cancer subject" means a subject who has been diagnosed with cancer.

The term "solid tumor subject" means a subject who has been diagnosed with a solid tumor cancer. In one embodiment, the solid tumor cancer is cholangiocarcinoma.

The term "hematologic malignancy subject" means a subject who has been diagnosed with a hematologic malignancy. In one embodiment, the hematologic malignancy subject is an AML subject. The term "AML subject" means a subject who has been diagnosed with AML. Methods for diagnosing AML are known to those of ordinary skill in the art, e.g., in Dohner H, et al., *Blood* 2017; 129: 424-447.

The terms "acute myeloid leukemia," "acute myelogenous leukemia," and "acute nonlymphocytic leukemia" are synonymous.

"Responsiveness to hematologic malignancy (e.g., AML) treatment" includes improvement in overall survival, partial response to treatment, long-term stable disease, or improvement in long-term survival characterized as complete remission (determined by less than 5% myeloblasts in bone marrow or the absence of circulating blasts), hematologic recovery (as evidenced by a peripheral blood absolute neutrophil count greater than 1,000 cells/μL and a platelet count greater than 100,000/μL, without the need for red blood cell transfusion, and the absence of extramedullary disease) (Bloomfield C D, et al., *Blood Revs.* 2018; 32: 416-425).

The term "IDH1 R132 mutation" is synonymous with "R132 IDH1 mutation," and refers to an IDH1 mutation at amino acid residue 132 in a subject's IDH1 gene., as determined, e.g., in the subject's nucleic acid (e.g., DNA).

The term "identified as having an IDH mutation" means that nucleic acid (e.g., DNA) from a human subject's tissue or cells has been analyzed to determine if the human subject has an IDH mutation (e.g., an IDH1 R132 mutation, an IDH2 R140 mutation or an IDH2 R172 mutation). In one embodiment, the human subject's blood, blood cells, bone marrow, bone marrow cells, lymph node, lymph node cells, lymphatic fluid or lymphatic fluid cells has been analyzed for an IDH mutation. In another embodiment, the human subject's solid tissue has been analyzed for an IDH mutation. In another embodiment, the human subject's solid tissue has been analyzed for an IDH mutation.

In the methods of the present invention, the party who identifies the human subject as having an IDH mutation (e.g., an IDH1 R132 mutation, an IDH2 R140 mutation or an IDH2 R172 mutation) can be different than the party that administers the first and second compounds. In one embodiment, the party who identifies the human subject as having an IDH mutation (e.g., an IDH1 R132 mutation, an IDH2 R140 mutation or an IDH2 R172 mutation) is different than the party that administers the first and second compounds.

Analytical methods identifying genetic mutations are known to those of ordinary skill in the art (Clark, O., et al., *Clin. Cancer. Res.* 2016; 22: 1837-42), including, but not limited to, karyotyping (Guller J L, et al., *J. Mol. Diagn.* 2010; 12: 3-16), fluorescence in situ hybridization (Yeung D T, et al., *Pathology* 2011; 43: 566-579), Sanger sequencing (Lutha, R et al., *Haematologica* 2014; 99: 465-473), metabolic profiling (Miyata S, et al., *Scientific Reports* 2019; 9: 9787), polymerase chain reaction (Ziai, J M and A J Siddon, *Am. J. Clin. Pathol.* 2015; 144: 539-554), next-generation sequencing (e.g., whole transcriptome sequencing) (Lutha, R et al., *Haematologica* 2014; 99: 465-473; and Wang H-Y, et al., *J. Exp. Clin. Cancer Res.* 2016; 35: 86).

The term "in combination with" means that a compound of Formula I is used, or is for use, in simultaneous, separate, or sequential combination with a Bcl-2 inhibitor in the treatment of cancer.

The terms "treatment," "treat," "treating," and the like, are meant to include slowing, stopping, or reversing the progression of cancer. These terms also include alleviating, ameliorating, attenuating, eliminating, or reducing one or more symptoms of a disorder or condition, even if the cancer is not actually eliminated and even if progression of the cancer is not itself slowed, stopped or reversed.

"Therapeutically effective amount" means the amount of a compound, or pharmaceutically acceptable salt thereof, administered to the subject that will elicit the biological or medical response of or desired therapeutic effect on a subject. A therapeutically effective amount can be readily determined by the attending clinician, as one skilled in the art, by the use of known techniques and by observing results obtained under analogous circumstances. In determining the effective amount for a subject, a number of factors are considered by the attending clinician, including, but not limited to: size, age, and general health; the specific disease or disorder involved; the degree of or involvement or the severity of the disease or disorder; the response of the individual subject; the particular compound administered; the mode of administration; the bioavailability characteristics of the preparation administered; the dose regimen selected; the use of concomitant medication; and other relevant circumstances.

The compounds administered in the method of the invention can optionally be formulated as pharmaceutical compositions administered by any route which makes the compounds bioavailable. In an embodiment, such compositions are formulated for oral administration. Such pharmaceutical compositions and processes for preparing the same are well known in the art. (See, e.g., *Remington: The Science and Practice of Pharmacy* (D. B. Troy, Editor, 21st Edition, Lippincott, Williams & Wilkins, 2006).

A "pharmaceutically acceptable carrier, diluent, or excipient" is a medium generally accepted in the art for the delivery of biologically active agents to mammals, e.g., humans.

It will be understood by one of ordinary skill in the art that compounds administered in the method of the invention are capable of forming salts. The compounds react with any of a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008).

"Pharmaceutically acceptable salts" or "a pharmaceutically acceptable salt" refers to the relatively non-toxic, inorganic and organic salt or salts of the compounds of the present invention (S. M. Berge, et al., "Pharmaceutical Salts", *Journal of Pharmaceutical Sciences*, Vol 66, No. 1, January 1977).

Materials and Methods

2-HG Inhibition Assay

Cell Line Construction.

MOLM14 wild-type human leukemia cells and a MOLM14 R132 construct cell line are generated by lentiviral transfection of MOLM14 cells using IDH1 WT (doxycycline inducible) pSLIK-IDH1-FLAG (Addgene Plasmid #66802) and IDH1 R132H (doxycycline inducible) pSLIK-IDH1-R132H-FLAG (Addgene Plasmid #66803), and is kindly provided by Dr. Jean-Emmanuel Sarry (Centre de Recherches en Cancérologie de Toulouse, UMR1037, Inserm, Université de Toulouse 3 Paul Sabatier, Toulouse, France; bioRxiv 749580; doi.org/10.1101/749580). MOLM14-WT and MOLM14-R132 mutant cells are seeded in 6 well plates (lx $10^6$/well) in 5 ml of complete RPMI medium containing 10% FBS (Sigma) and 1× Pen/Strep (Sigma). After induction with 2 μg/ml doxycycline, the cells are incubated in 37 degree for 4 days.

Cells are seeded in 12 wells plates (100,000 cells/well) in 1 mL, in triplicate. Cells are treated with 2 μg/ml doxycycline to induce IDH1 expression, then treated with DMSO, 0.1 or 1 μM Compound A, and incubated at 37 degrees C. for 4 days.

65 μL of media are collected and centrifuged, and 60 μL of the supernatant media are collected and frozen at −80 degrees C.

LCMS 2-HG Metabolite Analysis.

The effects of IDH1 inhibition on the concentrations of total 2-HG and (α-KG) are determined by liquid chromatography-mass spectrometry (LC-MS) analysis of cell culture supernatant. Calibration curves are prepared by spiking 2-HG and α-KG into cell culture media. The method utilizes derivatization with O-benzylhydroxylamine prior to analysis by LC-MS. Ten microliters of each standard or sample is placed into a deep-well 96-well plate and combined with 100 μL of internal standard solution containing 10 μM d5-2-hydroxyglutarate and 10 μM d6-α-KG. 50 μL of 1 M O-benzylhydroxylamine in pyridine buffer (8.6% pyridine, pH 5) and 50 μL of 1 M N-(3-dimethylaminopropyl)-N-ethylcarbodiimide hydrochloride (EDC) in pyridine buffer is added to each sample. The derivatization reaction proceeds at room temperature for one hour. Using a Beckman Biomek FX liquid handler 300 μL of ethyl acetate is added to each sample. Plates are sealed and vortexed for 5 minutes, and then centrifuged for 5 minutes at 4000 rpm on an Eppendorf 5810R centrifuge. 220 μL of the upper layer is transferred to a new 96-well plate. Samples are dried under heated nitrogen at 50° C. and reconstituted with 100 μL of methanol/water (1:1). One microliter of derivatized sample is injected onto an LC-MS system consisting of a Shimadzu Prominence 20A HPLC system and a Thermo Quantum Ultra™ triple quadrupole mass spectrometer. Analytes are separated on a Water XBridge™ C18 column (2.1×50 mm, 3.5 μm) with a flow rate of 0.6 mL/minute. Mobile phase A is 0.1% formic acid in water and mobile phase B is methanol. The gradient profile is: 0 minutes, 5% B; 2 minutes, 100% B; 4.00 minutes, 100% B; 4.1 minutes, 5% B; 5.50 minutes, stop. The mass spectrometer utilizes a HESI-II probe operated in positive ion selected reaction monitoring mode. Calibration curves are constructed by plotting analyte concentrations vs. analyte/internal standard peak area ratios and performing a quadratic fit of the data using a 1/concentration weighting with Xcalibur™ software. Analyte concentrations for the unknowns are back-calculated from the calibration curves.

In experiments performed essentially as described above, the results in Table 1 are obtained.

TABLE 1

| 2-HG (μM) | | |
|---|---|---|
| DMSO | 0.1 μM Compound A | 1 μM Compound A |
| 44.308 | 3.369 | 3.578 |
| 53.071 | 3.044 | 3.199 |
| 54.163 | 3.488 | 3.378 |

The results in Table 1 demonstrate that in the MOLM14 R132 cell line construct, Compound A inhibits 2-HG production by mutant IDH1.

Cell Viability Assay

MOLM14 wild-type and MOLM14 R132 cells are treated with 2 μg/ml doxycycline to induce expression of IDH1 WT and IDH1-R132H and then incubated at 37 degrees C. for 4 days. Cells are seeded in 4 (12 wells) plates at 10,000 cells/well in 1 mL growth media containing 2 ug/mL doxycycline.

Cells are treated with: DMSO (in triplicate), or with Compound A at 0, 125, 250, 500, 1000 nM (each in triplicate) as described in the following: After the initial induction described above, 0.5 mL media with 1× of doxycycline plus 1× Compound A or DMSO is added and incubated for 3 days. After the 3 days, another 0.5 mL aliquot of fresh media with 1×doxycyline plus 1×compound A or DMSO is added and incubated for 3 further days. Venetoclax (0, 25, 50, 100, 200 nM) is then added as a single agent or in combination with 1× Compound A. Two days later, cells are collected in flow cytometry filtered tubes, and processed for flow cytometry. Cells are washed with Annexin V Binding Buffer (ABB, 2 mL) [1 M Hepes buffer (10 mL), 5 M NaCl (28 mL), 1 M $CaCl_2$ (5 mL), $H_2O$ (957 mL)], and then centrifuged at 1500 rpm for 5 min. Cells are stained with ABB (50 μL), with APC Annexin V Antibody (1 μL, Biolegend cat #640941), and kept in the dark for 20 minutes. Cells are washed with ABB (2 mL) and centrifuged at 1500 rpm for 5 min. DAPI (Invitrogen cat #D3571) and counting beads (Invitrogen cat #C36950) are added in Annexin V binding buffer [DAPI (5 μL, 2 μg/mL)+counting beads (5 μL (520,000 beads per 50 μL))+ABB (150 μL)] in a total volume 160 μL/tube, then analyzed with a Gallios flow cytometer (Beckman Coulter). Cells collection is stopped when counting beads reach 250 beads per sample. Kalusa software is used for analysis. The percentage of gated Annexin V-negative/DAPI-negative cells constitutes % viable cells, while the percentage of Annexin V-positive cells constitutes % apoptosis.

In experiments performed essentially as described above, the results in Tables 2A-2C and 3 are obtained.

TABLE 2A

| Cell viability after treatment with Compound A | | | |
|---|---|---|---|
| Compound A (nM) | % Cell Viability | | |
| 0 | 96.63 | 96.2 | 96.25 |
| 125 | 93.72 | 95.14 | 94.27 |
| 250 | 93.34 | 94.27 | 94.41 |
| 500 | 93.66 | 93.92 | 94.15 |
| 1000 | 92.03 | 93.98 | 91.68 |

TABLE 2B

| % Cell viability after treatment with Venetoclax | | | |
|---|---|---|---|
| venetoclax (nM) | % Cell Viability | | |
| 0 | 96.63 | 96.2 | 96.25 |
| 25 | 76.09 | 81.78 | 77.84 |
| 50 | 76.91 | 80.63 | 78.78 |
| 100 | 70.42 | 76.91 | 73.78 |
| 200 | 55.2 | 59.27 | 56.31 |

TABLE 2C

| % Cell viability after treatment with Combination of Compound A and Venetoclax | | | |
|---|---|---|---|
| venetoclax (nM) and Compound A (nM), respectively | % Cell Viability | | |
| 0, 0 | 96.63 | 96.2 | 96.25 |
| 25, 125 | 69.03 | 76.03 | 74.44 |
| 50, 250 | 71.16 | 77.27 | 73.85 |
| 100, 500 | 60.22 | 66.97 | 63.16 |
| 200, 1000 | 27.26 | 34.96 | 27.25 |

The results in Tables 2A-2C demonstrate that the combination of venetoclax and Compound A results in further reduction in leukemic cell viability, relative to the level of leukemic cell viability of cells treated with either compound alone.

TABLE 3

| % Annexin V + as a measure of apoptosis | | | | | | | | | |
|---|---|---|---|---|---|---|---|---|---|
| Venetoclax (nM) and Compound A (nM), respectively | Compound A | | | Venetoclax | | | Compound A + Venetoclax | | |
| 0, 0 | 2.89 | 2.94 | 2.88 | 2.89 | 2.94 | 2.88 | 2.89 | 2.94 | 2.88 |
| 25, 125 | 5.56 | 4.3 | 5.12 | 19.1 | 15.93 | 19.16 | 26.41 | 19.75 | 22.89 |
| 50, 250 | 6.18 | 4.95 | 4.92 | 18.22 | 16.34 | 17.15 | 24.65 | 17.31 | 19.45 |
| 100, 500 | 5.82 | 5.23 | 5.19 | 24.62 | 18.98 | 22.98 | 30.57 | 28.46 | 26.32 |
| 200, 1000 | 7.2 | 5.51 | 7.52 | 41.67 | 35.73 | 41.22 | 69.28 | 55.11 | 67.71 |

The results in Table 3 demonstrate that the combination of venetoclax and Compound A results in an increased level of apoptosis in leukemic cells, relative to the level of apoptosis of cells treated with either compound alone.

AML-PDX Model

Male NSG mice (6-9 weeks of age, The Jackson Laboratory) are irradiated with 250 cGy and on the next day, injected intravenously with AML-PDX ($1\times10^6$ cells/100 μL). Peripheral blood is collected via the retro-orbital route and processed to measure hCD45+ cells by flow cytometry to confirm the establishment of leukemia.

When leukemia engraftment reaches more than 1%, mice are randomly grouped for treatment with vehicle, Compound A (10 mg/kg, daily oral gavage), venetoclax (50 mg/kg, oral gavage for 2 weeks on and 1 week off (2 cycles)) or the combination of venetoclax (50 mg/kg, oral gavage for 2 weeks on and 1 week off (2 cycles)) and Compound A (10 mg/kg, daily oral gavage). Additional dosing may be employed beyond the 2 cycles stated above based on the assessment of the level of residual disease remaining following 6 weeks of treatment.

Peripheral blood is collected once every two weeks via the retro-orbital route and processed to measure leukemia burden (% hCD33+/hCD45+ cells) by flow cytometry, and to measure differentiation (% hCD14+ cells percentage out of total hCD45+ cells)). Sixty-five μL stain/wash buffer (5% heat inactivated (HI)-FBS in DPBS) is added per tube, mixed up and down 3 to 4 times by pipette, and 100 μL of the blood suspension is transferred to 5 mL polypropylene tubes. The stains are added according to the manufacturer's instructions (anti-human CD33-APC (BD Biosciences cat #551378), anti-human CD14-PE-Cy7 (BD Biosciences cat #557742), anti-human CD45-APC-Cy7 (BD Biosciences cat #557833). The samples are incubated for 30 minutes at room temperature, protected from light. After the incubation, 1.5 mL 1× BD Lyse/Fix buffer (37° C., (BD #558049)) is added to each sample and incubated for 12 minutes at room temperature. The tubes are then centrifuged at 1500 RPMI for 5 minutes. BD Lyse/Fix solution is aspirated and the cell pellet washed with stain/wash buffer 2 times. Fixed cells are then resuspended in 200 μL stain/wash buffer then transferred to filtered flow tubes. Samples are analyzed on a Gallios Flow cytometer (Beckman, Texas) using standard flow cytometry principles and technique. Population gating and data analysis of percent population are performed in the Flow Jo software.

In experiments performed essentially as described above, the results in Tables 4 and 5 are obtained.

TABLE 4

| AML cell differentiation (% hCD14+ of hCD45+) | | | | |
|---|---|---|---|---|
| Animal | Vehicle | Compound A | Venetoclax | Compound A + Venetoclax |
| 1 | 20.6 | 63.6 | 37.7 | 55.2 |
| 2 | 25 | 64.1 | 26 | 68.5 |
| 3 | 34.6 | 51.7 | 40.7 | 56.7 |
| 4 | 20.7 | 58.9 | 32.6 | 54.1 |
| 5 | 19.4 | 44.1 | ND | 71.1 |
| 6 | ND | 58.3 | ND | ND |

ND: not determined (Data collected following 6 weeks of treatment)

TABLE 5

| Leukemic burden (% hCD33+hCD45+ of total white cells) | | | | |
|---|---|---|---|---|
| Animal | Vehicle | Compound A | Venetoclax | Compound A + Venetoclax |
| 1 | 74 | 51.5 | 10.1 | 6.4 |
| 2 | 86.5 | 65.6 | 63 | 15.2 |
| 3 | 92.6 | 85.1 | 14.1 | 5.25 |
| 4 | 93.3 | 81.9 | 54.9 | 4.73 |
| 5 | 92.6 | 87.8 | ND | 5.91 |
| 6 | ND | 88.5 | ND | ND |

ND: not determined (Data collected following 6 weeks of treatment)

The results in Tables 4 and 5 demonstrate that even though the combination of Venetoclax and Compound A does not result in an increased level of AML cell differentiation, the combination does result in a lower leukemia burden, relative to leukemia burden obtained using either compound alone, and reducing leukemia burden is a relevant clinical endpoint.

We claim:

1. A method of treating acute myeloid leukemia, comprising administering to a human cancer subject having an IDH mutation a therapeutically effective amount of (a) a first compound of the Formula:

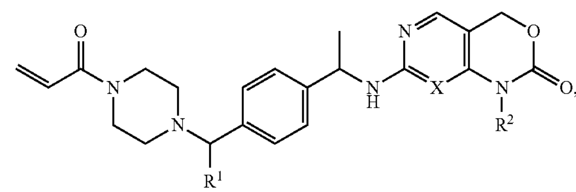

wherein:

$R^1$ is $—CH_2CH(CH_3)_2$, $—CH_2CH_3$, $—CH_2CH_2OCH_3$, or $—CH_2$-cyclopropyl;

$R^2$ is $—CH_3$ or $—CH_2CH_3$; and

X is N or CH, or a pharmaceutically acceptable salt thereof; and (b) a second compound that is venetoclax, or a pharmaceutically acceptable salt thereof.

2. The method of claim 1, wherein the IDH mutation is an IDH1 mutation.

3. The method of claim 2, wherein the IDH1 mutation is an IDH1 R132 mutation.

4. The method of claim 1, wherein the IDH mutation is an IDH2 mutation.

5. The method of claim 4, wherein the IDH2 mutation is an IDH2 R140 or IDH2 R172 mutation.

6. The method of claim 1, wherein in the first compound, X is N, or a pharmaceutically acceptable salt thereof.

7. The method of claim 1, wherein in the first compound X is N, $R^1$ is —$CH_2$-cyclopropyl, and $R^2$ is —$CH_2CH_3$, or a pharmaceutically acceptable salt thereof.

8. The method of claim 1, wherein the first compound is:

7-[[(1S)-1-[4-[(1R)-2-cyclopropyl-1-(4-prop-2-enoylpiperazin-1-yl)ethyl]phenyl]ethyl]amino]-1-ethyl-4H-pyrimido[4,5-d][1,3]oxazin-2-one;

7-[[(1S)-1-[4-[(1S)-2-cyclopropyl-1-(4-prop-2-enoylpiperazin-1-yl)ethyl]phenyl]ethyl]amino]-1-ethyl-4H-pyrimido[4,5-d][1,3]oxazin-2-one; or 1-Ethyl-7-[[(1S)-1-[4-[1-(4-prop-2-enoylpiperazin-1-yl)propyl]phenyl]ethyl]amino]-4H-pyrimido[4,5-d][1,3]oxazin-2-one;

or a pharmaceutically acceptable salt thereof.

9. The method of claim 1, wherein the first compound is of the Formula:

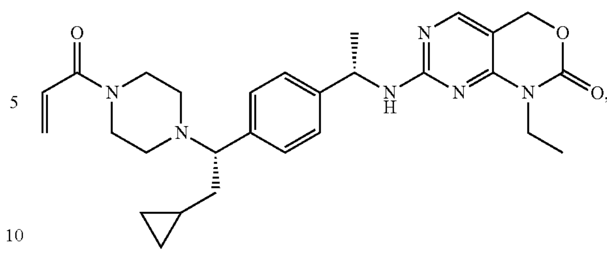

or a pharmaceutically acceptable salt thereof.

10. The method of claim 9, wherein the first compound is:

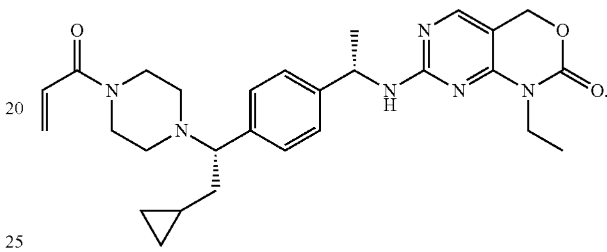

* * * * *